United States Patent [19]
Zajaczkowski

[11] Patent Number: 5,508,367
[45] Date of Patent: Apr. 16, 1996

[54] WATER-SOLUBLE PRESSURE SENSITIVE ADHESIVE

[75] Inventor: Michael J. Zajaczkowski, Yoe, Pa.

[73] Assignee: Adhesives Research, Inc., Glen Rock, Pa.

[21] Appl. No.: 399,876

[22] Filed: Mar. 7, 1995

Related U.S. Application Data

[63] Continuation-in-part of Ser. No. 272,827, Jul. 11, 1994, Pat. No. 5,395,907, which is a continuation-in-part of Ser. No. 158,405, Nov. 29, 1993, abandoned.

[51] Int. Cl.$^6$ .................................................. C08F 283/01
[52] U.S. Cl. .......................... 526/320; 526/304; 526/264; 526/307.5; 525/279; 525/283; 525/301; 525/312
[58] Field of Search ........................ 526/320, 304, 526/307.5, 264; 524/555, 558; 525/279, 283, 301, 312

[56] References Cited

U.S. PATENT DOCUMENTS

| | | | |
|---|---|---|---|
| 2,838,421 | 6/1958 | Sohl | 428/248 |
| 3,096,202 | 7/1963 | DeGroot Von Arx | 428/355 |
| 3,152,940 | 10/1964 | Abel et al. | 156/157 |
| 3,321,451 | 5/1967 | Gander | 526/287 |
| 3,441,430 | 4/1969 | Peterson | 428/354 |
| 3,556,835 | 1/1971 | Sorell | 428/354 |
| 3,660,147 | 5/1972 | Van Hoof et al. | 328/355 |
| 3,763,117 | 10/1973 | McKenna, Jr. et al. | 526/320 |
| 3,786,116 | 1/1974 | Milkovich et al. | 525/276 |
| 3,832,423 | 8/1974 | Milkovich et al. | 525/286 |
| 3,842,058 | 10/1974 | Milkovich et al. | 525/292 |
| 3,842,059 | 10/1974 | Milkovich et al. | 525/292 |
| 3,842,146 | 10/1974 | Milkovich et al. | 525/271 |
| 3,865,770 | 2/1975 | Blake | 524/187 |
| 3,890,292 | 6/1975 | Bohme et al. | 526/240 |
| 3,896,161 | 7/1975 | Borden et al. | 560/224 |
| 4,033,918 | 7/1977 | Hauber | 524/296 |
| 4,170,582 | 10/1979 | Mori et al. | 524/531 |
| 4,239,671 | 12/1980 | Fink et al. | 524/813 |
| 4,341,680 | 7/1982 | Hauber et al. | 525/293 |
| 4,388,432 | 6/1983 | Eskay | 524/388 |
| 4,413,080 | 11/1983 | Blake | 524/187 |
| 4,413,082 | 11/1983 | Gleichenhagen et al. | 524/243 |
| 4,442,258 | 4/1984 | Sunakawa et al. | 524/767 |
| 4,554,324 | 11/1985 | Husman et al. | 525/301 |
| 4,569,960 | 2/1986 | Blake | 524/145 |
| 4,952,655 | 8/1990 | Seelmann-Eggebert et al. | 526/318.4 |
| 4,992,501 | 2/1991 | Hanninen et al. | 524/272 |
| 5,084,348 | 1/1992 | Czech et al. | 428/355 |
| 5,094,912 | 3/1992 | Deibig et al. | 428/355 |
| 5,098,962 | 3/1992 | Bozich | 525/437 |
| 5,102,733 | 4/1992 | Zawadzki | 428/343 |
| 5,125,995 | 6/1992 | D'Haese et al. | 156/155 |
| 5,141,810 | 8/1992 | Ranade et al. | 428/350 |
| 5,183,841 | 2/1993 | Bernard | 524/272 |
| 5,196,504 | 3/1993 | Scholz et al. | 526/318.4 |
| 5,229,447 | 7/1993 | Miyajima et al. | 524/377 |
| 5,270,111 | 12/1993 | D'Haese et al. | 428/356 |
| 5,296,512 | 3/1994 | Beier et al. | 523/111 |
| 5,319,020 | 6/1994 | Rosenski et al. | 524/762 |
| 5,326,644 | 6/1994 | Scholz et al. | 428/514 |
| 5,332,607 | 7/1994 | Nakamura et al. | 428/40 |
| 5,380,779 | 1/1995 | D'Haese | 524/272 |
| 5,395,907 | 3/1995 | Zajaczkowski | 526/320 |

FOREIGN PATENT DOCUMENTS

| | | |
|---|---|---|
| 063037 | 10/1982 | European Pat. Off. |
| 147067 | 7/1985 | European Pat. Off. |

OTHER PUBLICATIONS

Chemical Abstracts and Registry, Abstract No. 100:52757 and corresponding R.N.'s and JP 58 108 278.

*Primary Examiner*—Mark Nagumo

[57] ABSTRACT

A water-soluble or water-dispersible pressure sensitive adhesive is provided comprised of a normally-tacky copolymer of a water-soluble base monomer and a water-soluble or water-dispersible macromer. In a preferred embodiment, the water-soluble base monomer comprises a carboxylic hydroxyalkyl ester monomer and the water-soluble macromer comprises an ethoxylated or propoxylated hydroxyalkyl (meth)acrylate.

22 Claims, No Drawings

WATER-SOLUBLE PRESSURE SENSITIVE ADHESIVE

CROSS REFERENCE TO RELATED APPLICATIONS

The present application is a continuation-in-part application of U.S. patent application Ser. No. 08/272,827, filed Jul. 11, 1994, now U.S. Pat. No. 5,395,907, issued Mar. 7, 1995, which is a continuation-in-part of application Ser. No. 158,405, filed Nov. 29, 1993, now abandoned.

BACKGROUND OF THE PRESENT INVENTION

The present invention is directed to a water-soluble or water-dispersible normally tacky pressure sensitive adhesive.

In papermaking and printing processes the ends of the paper rolls are spliced together to enable the formation of endless paper webs. Splicing of paper within a roll is also undertaken when the paper is cut to remove defective portions. For these purposes, it has been customary to use a repulpable pressure sensitive adhesive-based splicing tape. As various portions of the paper roll or web are cut out and recycled to the paper-making process, it is important for any adhesive which is used in the splice to be readily water-soluble or repulpable (i.e., readily disperses or dissolves in water during a pulping process) so as to not contaminate or discolor the paper which is produced upon being recycled. It is also important for the adhesive splice to be strong enough to resist web failure during the papermaking process or printing process as well as the ability to withstand elevated processing (such as printing) temperatures that may be encountered.

Off-machine paper coating processes also require the use of splicing tapes that exhibit the requisite tack, temperature resistance, and humidity resistance. It would also be desirable for such splicing tapes to exhibit repulpability. However, to date, few commercially acceptable splicing tapes exist that meet the stringent demands of off-machine coaters which subject the tape to excess amounts of water during the coating process as well as elevated temperatures. Also, to date, no commercially-acceptable repulpable splicing tape has been formed that may be satisfactorily employed in off-machine coaters.

Splicing tapes also frequently contribute to a failure in the splice in the paper web as a result of the combination of the speed of the web and the fact that the spliced web is eventually collected in the form of a roll and the splice is caused to conform to the curved surface of the roll. Such prior art splicing tapes employ an adhesive that is sufficiently inelastic such that the splice is incapable of withstanding the rigors encountered during rolling of the web. Such splicing failures contribute to significant inefficiency and expense, as such splice failures must be repaired.

A need also exists for pressure sensitive adhesive labels which can be easily removed from containers or other surfaces to which the adhesive-backed label has been applied. This need exists in particular with respect to containers made from plastic or glass which are intended to be reused. It is accordingly desirable to provide labels which are easily removable by means of water, which labels are most preferably water-soluble or dispersible.

Various attempts have been made to solve such problems as discussed in U.S. Pat. Nos. 3,441,430; 3,556,835; 3,660,147; 4,413,080; 4,413,082; 4,992,501; 5,084,348; 5,094,912; 5,098,962; 5,102,733; 5,125,995; 5,141,810; 5,183,841; 5,196,504; and WO 93/06184. Such alternative solutions require, for example, the use of added tackifying agents or result in adhesives which are soluble in aqueous alkaline solutions. However, the prior art reliance upon water-soluble tackifying agents to impart the required water-solubility for the pressure sensitive adhesive (especially in repulpable adhesives) results in several disadvantages. The prior art relies on the ability of the tackifier to be removed from the adhesive composition in the presence of water (with the intended result that the composition cannot serve as an adhesive due to loss of tack). However, under conditions of high humidity the tackifier may migrate from the adhesive to the adjacent substrate (such as the paper roll). The paper may, as a result, be spotted or discolored by the migrating tackifier. In order to avoid such a consequence, repulpable adhesive tapes are generally sealed in bags to protect against excess humidity. This packaging requirement is costly and burdensome, and as yet unavoidable.

An additional disadvantage that exists with regard to tackified repulpable pressure sensitive adhesives is the fact that the tackified base polymer is itself non-water soluble. As a result the potential for contamination exists due to the presence of the non-water soluble adhesive once the tackifier is solubilized.

Thus, a need exists for a pressure sensitive adhesive which exhibits enhanced water-soluble or water-dispersible characteristics without the need for added tackifying agents and whose water-solubility may be tailored for specific applications. It is also desirable to provide a repulpable water-soluble or water-dispersible pressure sensitive adhesive which is resistant to loss of adhesive properties upon exposure to conditions of high humidity and high temperature, and which does not serve as a source of contamination or discoloration. It is also desirable to provide a high performance pressure sensitive adhesive that is also water-soluble or water-dispersible.

OBJECTS AND SUMMARY OF THE PRESENT INVENTION

It is one object of the present invention to provide a water-soluble or water-dispersible pressure sensitive adhesive.

It is further an object of the present invention to provide a water-soluble or water-dispersible pressure sensitive adhesive which may be used in the absence of tackifiers or plasticizers.

It is still further an object of the present invention to provide a water-soluble pressure sensitive adhesive which exhibits high performance adhesive properties as well as humidity and temperature resistance and water dispersibility.

It is also an object of the present invention to provide a repulpable pressure sensitive adhesive.

It is further an object of the present invention to provide adhesive-coated backing materials such as sheets or tapes coated with such water-soluble or water-dispersible adhesives.

In accordance with the present invention, there is thus provided a water-soluble or water-dispersible normally-tacky pressure sensitive adhesive comprised of a graft copolymer comprised of one or more water-soluble base monomers A and a water-soluble or water-dispersible macromer C, and optionally one or more B monomers copolymerized with said A monomer, wherein said base monomer A comprises a vinyl monomer capable of forming a hydrophilic polymer and having a $T_g$ <20° C., said optional monomer B being capable of forming a hydrophilic or hydrophobic polymer, and said C macromer forming polymeric sidechains on said graft copolymer, with the provisos that when said C macromer is present in an amount of at least 45 percent by weight, then at least 5 percent by weight of a B monomer having a $T_g$ >20° C. is present, and when said C macromer is present in an amount of 35 percent by weight or less, then at least 5 percent by weight of a B monomer having a $T_g$ <0° C. is present, and wherein any B monomer present, if hydrophobic, is present in an amount up to 25 percent by weight, based on the total weight of the components A, B and C, said adhesive exhibiting a tackifier or plasticizer-free Polyken probe back value of at least 300 gm/cm$^2$ as determined by ASTM 02979, a peel adhesive value of at least 20 oz/in as determined by PSTC 1, and a shear holding value of greater than 5 minutes as determined at 500 grams according to PSTC 7.

In accordance with a preferred embodiment of the present invention, there is also provided a water-soluble or water-dispersible normally tacky pressure sensitive adhesive comprised of a graft copolymer comprised of one or more water-soluble base monomers A and a water-soluble or water-dispersible macromer C, and optionally one or more B monomers copolymerizable with said A monomer, wherein said base monomer A comprises a vinyl monomer capable of forming a hydrophilic polymer and having a $T_g$ <20° C., said optional monomer B is capable of forming a hydrophilic or hydrophobic polymer, and said macromer C forming polymeric sidechains on said graft copolymer and comprising a hydrophilic macromer represented by the formula:

$$X\text{-}(Y)_p\text{-}(O\text{-}C_mH_{2m})_n\text{-}R$$

wherein X is a moiety copolymerizable with monomers A and B or capable of attachment to polymerized monomers A and B, Y is a divalent linking group, R is a terminal group; and in which m is an integer of from 2 to 6, n is an integer of from 5 to 300, and p is 0 or 1.

In accordance with the present invention, there is also provided an adhesive-coated tape or sheet material having a portion of at least one surface thereof coated with the adhesive of the present invention.

DETAILED DESCRIPTION OF THE INVENTION

The normally-tacky pressure sensitive adhesive of the present invention comprises a water-soluble or water-dispersible graft copolymer of at least one water-soluble base monomer and a hydrophilic macromer. The term "tacky" is intended to mean that the polymer is sticky by nature and exhibits adhesion upon contact with a surface.

The water-soluble base monomer A comprises a vinyl monomer capable of forming a hydrophilic polymer and having a $T_g$<20° C. In general, such monomers comprise hydroxy (lower) alkyl acrylates, hydroxy (lower) alkyl methacrylates, dihydroxy (lower) alkyl methacrylates, etc. Exemplary water-soluble base monomers include but are not limited to hydroxyethyl acrylate, hydroxypropyl acrylate, hydroxybutyl acrylate, hydroxybutyl methacrylate, as well as alkyl vinyl ethers and hydroxy alkyl vinyl ethers (wherein the alkyl group has up to 5 carbon atoms). One or more of the water-soluble A monomers may be employed.

The macromer C forms polymeric sidechains on the graft copolymer. The macromer C is hydrophilic by nature (i.e., the macromer is water-soluble or water-dispersible).

The macromer may be represented by the formula X-(Y)$_p$-Z-R wherein X is a moiety copolymerizable with monomers A and B or, in the alternative, capable of attachment to polymerized monomers A and B, Y is a divalent linking group, Z is a water-soluble or water-dispersible homo- or polymeric moiety essentially unreactive at copolymerization conditions, R is a terminal group, and p is 0 or 1.

More specifically, the X moiety is an unsaturated polymerizable moiety the composition of which is not critical. The X moiety may be, for example, when intended to be copolymerizable with monomers A and B, simply a vinyl group of the formula CHR=CR$^1$— where R is hydrogen or COOH and R$^1$ is hydrogen or alkyl such as methyl. Other exemplary X moieties include but are not limited to methacryloyl, maleoyl, itaconoyl, crotonoyl, unsaturated urethane moiety, methacrylamido and moieties of the formula $$CH_2=CHCH_2O\text{—}.$$

The X moiety may comprise an amine or alcohol moiety (such as a monohydroxyl or monoamine moiety) which permits attachment of the macromer to a suitable functionality on previously-polymerized monomers A and B. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A preferred Y divalent linking group is

or a linking group which incorporates such a moiety.

Additional Y linking groups which may be employed in connection with the present invention include but are not limited to the following moieties:

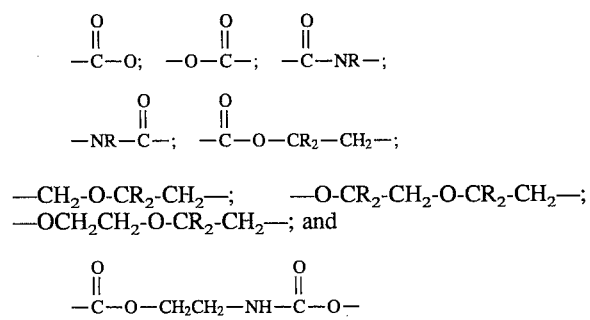

CR$_2$-CH$_2$—; where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842,058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyvinyl caprolactam radical, polymethylvinyl ether radical or mixtures thereof. Exemplary C macromers formed from such radicals include but are not limited to ethoxylated or propoxylated hydroxy(lower)alkyl meth(acrylate) and polymethylvinyl ether mono(meth)acrylate. The molecular weight of the macromer used in the present invention is not critical but will generally range from about 300 to about 50,000, and preferably from about 300 to 3,000.

The hydrophilic macromer C is more preferably represented by the formula:

wherein X and Y are as defined above and R represents a terminal group; and in which m is an integer of from 2 to 6 and n is an integer of from 5 to 300. More specifically, macromer C is advantageously an ethoxylated or propoxylated hydroxy(lower)alkyl (meth)acrylate represented by the formula:

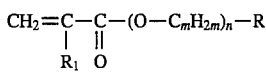

wherein $R_1$ is hydrogen or $C_{1-5}$ alkyl and R is a terminal group. Preferably, m is 2 or 3 and n is 5 to 30, and R is OH or $C_{1-5}$ alkyl.

The Z moiety is preferably comprised solely of one or more hydrophilic monomer radicals to ensure that the resulting macromer is water-soluble or water-dispersible. However, the Z moiety may also be a copolymer of hydrophilic and hydrophobic monomers, with any copolymerized hydrophobic portion being present in an amount insufficient to render the resulting macromer water-insoluble or non-water-dispersible. Desirably, any non-hydrophilic portion employed in such a copolymer is present in an amount of less than 50 percent by weight based on the weight of the macromer, and preferably less than 30 percent by weight.

The macromer C may employ a variety of terminal groups R. While the terminal group may typically be OH or $C_{1-5}$ alkyl, it may be desirable to select a terminal group based on the functional character of the terminal group. For instance, suitable terminal groups include but are not limited to (1) acid/ionic groups such as carboxyl, phosphate or sulfate groups, (2) hydrophobic groups such as lower alkyl, phenyl or substituted phenyl, and (3) hydrophilic groups such as hydroxyl or amine groups.

Depending upon the terminal group employed, ionic end groups may be used to provide pH-dependent solubility characteristics for the copolymer. Hydrophobic terminal groups may be used to reduce the water solubility of the copolymer.

Other physical properties or characteristics of the copolymer may be modified by selection of suitable terminal groups. Ionic terminal groups may be used to provide a desired degree of crosslinking; for example, by neutralizing acid moieties with metal hydroxides. High temperature performance may be enhanced by incorporating an acid functionality in conjunction with a ditertiary amine. Aqueous solution viscosities may be influenced by the presence of ionic terminal groups.

As discussed above, one or more polymerizable B monomers may be incorporated in the copolymer which B monomer(s) is copolymerizable with the A monomer. Such additional B monomer(s) may be either hydrophilic or hydrophobic. In the event that a reduced degree of water solubility of the adhesive is acceptable (such as for non-repulp applications), it may be advantageous to incorporate a hydrophobic B monomer in an amount that renders the polymer composition either water-insoluble or reduces the extent or degree of water solubility of the polymer. For instance, the presence of from 30–40 percent by weight of a hydrophobic B monomer in the composition will render the adhesive non-soluble but water-dispersible or, in the alternative, insoluble (depending upon the amount of the hydrophobic B monomer employed). For applications where it is desirable to enhance the water-solubility or water-dispersibility of the adhesive, it is preferable for the B monomer, if hydrophobic, to be present in an amount of 25 percent by weight or less, and most preferably 20 percent by weight or less. Generally, in a repulp application, the B monomer will be present in an amount of 15 percent by weight or less.

Exemplary optional B monomers include water-soluble vinyl monomers having at least one nitrogen atom. Such monomers (each of which exhibit a $T_g$ of >20° C.) include but are not limited to N-mono-substituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide, and N,N-dihydroxyethylacrylamide, etc.

Other optional B monomers may include, for example, various vinyl monomers such as acrylic and methacrylic acid, methoxyethyl acrylate or methacrylate, ethyoxyethyl acrylate or methacrylate, methyl acrylate or methacrylate, ethyl acrylate or methacrylate, propyl acrylate or methacrylate, glycerol acrylate or methacrylate, hydroxyethyl methacrylate, hydroxypropyl methacrylate, vinyl pyrrolidone and vinyl caprolactam (each of which also exhibit a $T_g$ of >20° C.). Monomeric acrylic or methacrylic acid esters of a non-tertiary alcohol having from 4–12 carbon atoms on average, and preferably from 4–8 carbon atoms, such as n-butyl acrylate or methacrylate, etc. are also suitable B monomers, with such monomers exhibiting a $T_g$ of <0° C. One or more B monomers may be employed.

Preferably, said A monomer is present in an amount of from 25 to 70 percent by weight, said optional B monomer is present in an amount of from 0 to 40 percent by weight (based on combined weights of hydrophilic and/or hydrophobic B monomers), and said C macromet is present in an amount of from 10 to 65 percent by weight, and preferably 30 to 60 percent by weight, based on the total weight of the respective components A, B and C in the composition. If both hydrophilic and hydrophobic B monomers are present, the amount of the hydrophobic B monomer present is preferably insufficient to exceed 25 percent by weight of the total weight of the monomers A, B and C.

Preferably, the composition contains at least about 35 percent by weight of the A monomer and at least about 30 percent by weight of the C macromer. Most preferably, at least about 40 percent by weight of the A monomer is present. Most preferably, at least 35 percent by weight of the C macromer is present.

By way of further proviso, when the C macromer is present in an amount of at least 45 percent by weight, then at least 5 percent by weight of a B monomer having a $T_g$ of >20° C. is present, and when the C macromer is present in an amount of 35 percent by weight or less, then at least 5 percent by weight of a B monomer having a $T_g$ of <0° C. is present in order to ensure that the composition of the present invention exhibits satisfactory adhesive properties of probe tack, peel and shear.

If less than 30 percent by weight of the C macromer is employed, it may be necessary to incorporate a water-soluble tackifier or plasticizer into the composition to provide sufficient tack. Exemplary tackifiers include polyethylene glycol, polypropylene glycol, and suitable polyoxyethylene-based compounds. Suitable polyoxyethylene-based tackifiers are disclosed at column 6 of U.S. Pat. No. 4,413,080, herein incorporated by reference in its entirety. Such tackifiers, if present, may be employed in an amount of up to about 50 percent by weight, based on the total weight of the composition. While the use of a tackifier or plasticizer in repulp applications is not generally seen to be an advantage, it is possible that the tackifier or plasticizer may actually be used with advantage in non-repulp applications, and may accordingly be present in the composition as found appropriate.

Most preferably, in order to provide a "tackifier-free" or "plasticizer-free" adhesive for use in repulp applications, the weight ratio of C macromer to total weight of monomers A and B ranges from 35:65 to 65:35, with it being further preferred that the C macromer be present in a weight ratio of 40:60 to 50:50 based on the weight of C macromer to total weight of A and B monomers.

The weight average molecular weight of the resulting polymer is preferably at least 18,000, and may be as high as 100,000–200,000, with the upper limit of molecular weight being that which detracts from the desired water-solubility of the polymer.

By way of advantage, the repulpable pressure sensitive adhesive of the present invention enables the use of a water-soluble tackifier or plasticizer to be avoided (thus avoiding potentially-damaging tackifier migration problems). The C macromer itself serves to "tackify" the adhesive composition while avoiding problems associated with migration of the tackifying component as in the prior art. This provides the further advantage that such adhesives, while water soluble, do not need to be protected from excess humidity (such as by bagging) as the adhesive is surprisingly humidity-resistant. The lack of a need to protect such adhesives from the ambient environment results in less waste, greater economic efficiency, and no need for special handling.

A still additional advantage is that the adhesive composition of the present invention employs a water-soluble base polymer in contrast to the water-insoluble base polymer generally used in prior art repulpable compositions. The pressure sensitive adhesive of the present invention is accordingly substantially if not completely water-soluble or dispersible, a result not heretofore accomplished by the prior art adhesive compositions. Little, if any, adhesive residue remains to serve as a potential contaminant upon contact of the adhesive with excess amounts of water.

As noted above, the copolymer composition of the present invention may be prepared by any conventional polymerization technique, including (1) free radical initiated copolymerization of components A and C and optionally B in the presence of a solvent, and (2) attachment of the macromer C graft to a preformed backbone polymer formed from copolymerized monomer A optionally copolymerized with monomer B via reaction with a suitable functional group on the backbone polymer subsequent to formation of same. Suitable copolymerization temperatures range from about 20° C. to about 150° C. for periods of time of from 2 to 24 hours until the desired degree of conversion occurs. Upon completion of the copolymerization process, the solvent is removed and a tacky copolymer results having acceptable adhesive properties. If desired, a suitable cross-linking agent may be employed to increase the molecular weight of the adhesive if desired.

The adhesive of the present invention may be used in association with a variety of body members to provide an adhesive assembly. For example, the body member may be in the form of a backing material coated on at least one side thereof with the adhesive to provide an adhesive-backed sheet film or tape. Exemplary backing materials used in the production of such a product include but are not limited to flexible and inflexible backing materials conventionally employed in the area of pressure sensitive adhesives, such as creped paper, kraft paper, fabrics (knits, non-wovens, wovens), foil and synthetic polymer films such as polyethylene, polypropylene, polyvinyl chloride, poly(ethylene terephthalate) and cellulose acetate, as well as glass, ceramics, metallized polymer films and other compatible sheet or tape materials.

Preferably, in order to enable the adhesive assembly to exhibit "repulpable" properties, a backing material is employed which is water-dispersible. In such an instance, the backing material is generally comprised of a paper layer, such as kraft paper or tissue paper, although any water-dispersible backing layer may be employed. For instance, water-soluble polymeric materials such as polyvinyl alcohol can also be used as a backing layer.

The body member (e.g., in sheet form) may be coated in any conventional manner with the adhesive composition of the present invention, such as by roll coating, spray coating, extrusion coating, co-extrusion coating, hot melt coating by use of conventional coating devices. When appropriate, the adhesive of the present invention may be applied as a solution to at least one surface of the body member and the solvent subsequently removed to leave a tacky adhesive residue on the body member. The adhesive may be applied to the body member either in the form of a continuous layer or in discontinuous form.

The resulting pressure sensitive adhesive-backed body member may take many forms, such as tapes, patches, strips, labels, etc., with the choice and form ultimately being determined by the end use contemplated.

The pressure sensitive adhesive of the present invention may be used in a wide variety of commercial applications. An adhesive tape formed in accordance with the present invention may be used-as a splicing tape in paper making, printing and off-machine coating processes while providing advantages not provided by other commercially-available adhesive tapes. An adhesive tape produced according to the present invention provides a combination of high performance characteristics such as tack, water and temperature resistance in combination with water-solubility and water-dispersibility not heretofore provided by present commercially-available alternatives. In contrast to prior art adhesive tapes, the adhesive of the present invention does not sacrifice performance to provide water-soluble or water-dispersible characteristics.

Advantageously, splicing tape produced in accordance with the present invention is also resistant to splicing failures during formation of rolls of spliced paper webs. This resistance to splice failure is believed due to the greater ability of the pressure sensitive adhesive to withstand the rigors of the web rolling process due to its rubbery nature due to the low $T_g$ of the adhesive.

The pressure sensitive adhesive of the present invention exhibits a tackifier-free Polyken probe tack value of at least 300 gms/cm$^2$ and a peel adhesion value of at least 20 oz/in. Advantageously, the Polyken probe tack value of the adhesive of the present invention will range from about 400 to 1500 gm/cm$^2$ as determined by ASTM D2979, land the peel adhesion value of the adhesive will range from 30 to 100 oz/in. as determined by PSTC 1. Preferably, the adhesive of the present invention exhibits a shear holding value of greater than 5 minutes (and preferably greater than 10 minutes) as determined at 500 grams according to PSTC 7.

The invention will be discussed in conjunction with the following examples, which are merely illustrative of the present invention and not intended to in any way limit the scope of the invention. The following Examples demonstrate the use of a water-soluble pressure sensitive adhesive which exhibits desirable characteristics such as peel, tack, shear and water solubility in the production of a repulpable pressure sensitive adhesive tape.

EXAMPLE 1

180.13 grams of ethyl acetate and 120.09 grams of isopropyl alcohol (as solvents) were charged to a 1-liter reaction vessel. To the charged material, 18.33% of the monomers identified below were added. Under a nitrogen atmosphere, the batch was heated to 71°–77° C. and 1.27 grams of VAZO-52 (polymerization initiator) were added. The reactants were allowed to polymerize for 20 minutes to produce a seed polymer capable of solvating the remaining reactants. Single stage polymerization was found to yield a non-processable gel, which result is avoided by the two-step polymerization using a seed reaction. The remaining 81.67% of the monomer mix along with 0.75 grams of benzoyl peroxide were added to the reaction mix over 2 hours while maintaining a reaction temperature of 71°–77° C. The reactants were polymerized until all monomers were consumed. The reactor feed mix consisted of the following components:

|  | Amount (Grams) |
| --- | --- |
| Monomers |  |
| HEMA-10 (macromer) | 114.09 |
| HEMA-5 (macromer) | 26.34 |
| Hydroxy Ethyl Acrylate (A monomer) | 83.88 |
| Hydroxy Propyl Acrylate (A monomer) | 100.67 |
| Acrylamide (B monomer) | 9.06 |
| Solvents |  |
| Ethyl acetate | 180.13 |
| Isopropyl alcohol | 120.09 |

Note:
HEMA-5,10 are 5 and 10 mole ethoxylates of hydroxy ethyl methacrylate (produced by BIMAX, INC.)
VAZO-52: Dupont trade name for free radical initiatoris 2,2'-azobis (2,4-dimethylpentanenitrile).

The thus-produced "tackifier-free" water-soluble adhesive composition was coated onto a conventional release sheet and dried to remove the solvent and provide a layer of pressure sensitive adhesive of a weight of 1 oz/yd$^2$. Tissue paper was then applied over the adhesive surface after which a second layer of adhesive having the same coated weight was applied to the reverse side of the tissue by contacting the tissue with adhesive on another release sheet. A double faced tape was thus produced having a water-soluble pressure sensitive adhesive thereon which tape readily dissolves or disperses in water.

EXAMPLE 2

The procedure of Example 1 was repeated using the following reactor feed components to produce a tackifier-free water-soluble pressure sensitive adhesive:

|  | Amount (Grams) |
| --- | --- |
| Monomers |  |
| HEMA-10 (macromer) | 134.22 |
| Hydroxy Ethyl Acrylate (A monomer) | 97.31 |
| Acrylamide (B monomer) | 9.06 |
| Butyl Acrylate (B monomer) | 57.04 |
| Vinyl Pyrrolidone (B monomer) | 20.13 |
| Acrylic Acid (B monomer) | 13.42 |
| Solvents |  |
| Ethyl acetate | 150.11 |
| Isopropyl alcohol | 150.11 |

EXAMPLE 3

The procedure of Example 1 was repeated using the following reactor feed components to produce a tackifier-free water-soluble pressure sensitive adhesive:

|  | Amount (Grams) |
| --- | --- |
| Monomers |  |
| HEMA-10 (macromer) | 113.50 |
| Hydroxy Ethyl Acrylate (A monomer) | 107.38 |
| Acrylamide (B monomer) | 6.56 |
| Butyl Acrylate (B monomer) | 54.73 |
| Vinyl Pyrrolidone (B monomer) | 40.25 |
| Acrylic Acid (B monomer) | 13.12 |
| Solvents |  |
| Ethyl acetate | 180.13 |
| Isopropyl alcohol | 120.09 |

EXAMPLE 4

The procedure of Example 1 was repeated using the following reactor feed components to produce a tackifier-free water-soluble pressure sensitive adhesive:

|  | Amount (Grams) |
| --- | --- |
| Monomers |  |
| HEMA-10 (macromer) | 134.22 |
| Hydroxy Ethyl Acrylate (A monomer) | 97.31 |
| Hydroxy Propyl Acrylate (A monomer) | 40.27 |
| Acrylamide (B monomer) | 10.06 |
| Butyl Acrylate (B monomer) | 23.56 |
| Vinyl Pyrrolidone (B monomer) | 10.06 |
| Acrylic Acid (B monomer) | 10.06 |
| Solvents |  |
| Ethyl acetate | 160.11 |
| Isopropyl alcohol | 140.11 |

EXAMPLE 5

The procedure of Example 1 was repeated using the following reactor feed components to produce a tackifier-free water-soluble pressure sensitive adhesive:

|  | Amount (Grams) |
| --- | --- |
| Monomers |  |
| HEMA-10 (macromer) | 268.43 |
| Hydroxy Ethyl Acrylate (A monomer) | 181.20 |

-continued

| | Amount (Grams) |
|---|---|
| Hydroxy Propyl Acrylate (A monomer) | 181.20 |
| Acrylamide (B monomer) | 20.13 |
| Acrylic Acid (B monomer) | 20.13 |
| Solvents | |
| Ethyl acetate | 345.25 |
| Isopropyl alcohol | 255.19 |

EXAMPLE 6

94.5 grams of ethyl acetate and 130.5 grams of isopropyl alcohol (or solvents) were charged to a 1-liter reaction vessel. To the charge, 18.33% of the monomers identified below were added. Under a nitrogen atmosphere, the batch was heated to 71°–77° C. and 0.94 grams of VAZO-52 (polymerization initiator) were added. The reactants were allowed to polymerize for 20 minutes. The remaining 81.67% of the monomer mix along with 0.50 grams of benzoyl peroxide were added to the reaction mix over 1 hour while maintaining a reaction temperature of 71°–77° C. The reactants were polymerized until all monomers were consumed (123.75 grams of isopropyl alcohol were added to reduce viscosity). The monomer feed consisted of the following:

| Monomers | % of Monomers | Amount (Grams) |
|---|---|---|
| HEMA-10 (macromer) | 38.13 | 90.00 |
| 2-Ethyl-2-Oxazoline (macromer) | 4.66 | 11.00 |
| Hydroxy Ethyl Acrylate (A monomer) | 23.83 | 56.25 |
| Hydroxy Propyl Acrylate (A monomer) | 10.97 | 25.88 |
| Vinyl Pyrrolidone (B monomer) | 4.77 | 11.25 |
| Vinyl Caprolactam (B monomer) | 4.77 | 11.25 |
| Butyl Acrylate (B monomer) | 12.87 | 30.37 |

The presence of the 2-ethyl-2-oxazoline macromet (5000 mw) enhanced both the cohesive strength and the high temperature performance of the tackifier-free water-soluble pressure sensitive adhesive.

EXAMPLE 7

The procedure of Example 6 was repeated with the exception that the 2-ethyl-2-oxazoline macromer was not employed:

| Solvents | Amount (Grams) |
|---|---|
| Ethyl Acetate | 189.00 |
| Isopropyl Alcohol | 261.00 |

| Monomers | % of Monomers | Amount (Grams) |
|---|---|---|
| HEMA-10 (macromer) | 40.00 | 179.98 |
| Hydroxy Ethyl Acrylate (A monomer) | 25.00 | 12.50 |
| Hydroxy Propyl Acrylate (A monomer) | 11.50 | 52.29 |
| Vinyl Pyrrolidone (B monomer) | 5.00 | 22.55 |
| Vinyl Caprolactam (B monomer) | 5.00 | 22.55 |
| Butyl Acrylate (B monomer) | 13.50 | 60.76 |

EXAMPLE 8

Ethyl acetate (25 grams) and isopropyl alcohol (75 grams) (as solvents) were charged to a reaction vessel. To the charge, 19.86% of the monomers identified below were added. Under a nitrogen atmosphere, the batch was heated to 70°–73° C. and 0.94 grams of VAZO-52 (polymerization initiator) were added together with 100 grams of additional solvent mixture. The reactants were allowed to polymerize for 20 minutes. The remaining 80.14% of the monomer mix along with benzoyl peroxide catalyst were added to the reaction mix over 1 hour while maintaining a reaction temperature of 70°–73° C. The reactants were polymerized until all monomers were consumed. The monomer feed consisted of the following:

| Monomers | % of Monomers | Amount (Grams) |
|---|---|---|
| HEMA-10 (macromer) | 40.00 | 90.00 |
| HEMA-5 | 5.00 | 11.00 |
| Hydroxy Ethyl Acrylate (A monomer) | 22.75 | 56.25 |
| Hydroxy Propyl Acrylate (A monomer) | 8.75 | 25.88 |
| Vinyl Pyrrolidone (B monomer) | 3.50 | 11.25 |
| Vinyl Caprolactam (B monomer) | 3.50 | 11.25 |
| Butyl Acrylate (B monomer) | 15.00 | 30.37 |
| Acrylic acid (B monomer) | 1.50 | |

Upon completion of the reaction, the reaction product is cooled and discharged from the reactor. Before coating on a backing material, 0.15% a cross-linking agent (an aziridine compound such as Hoechst Celanese XAMA-7) is added to the product to increase the temperature resistance of the adhesive.

What is claimed is:

1. A pressure sensitive adhesive comprised of a water-soluble or water dispersible normally-tacky graft copolymer comprised of one or more water soluble base monomers A and water soluble or water dispersible macromer C, and optionally one or more B monomers copolymerized with said A monomer, wherein said base monomer A comprises a vinyl monomer capable of forming a hydrophilic polymer and having a $T_g$ <20° C., said optional monomer B being capable of forming a hydrophilic or hydrophobic polymer, and said C macromer forming polymeric sidechains on said graft copolymer, with the provisos that when said C macromer is present in an amount of at least 45 percent by weight, then at least 5 percent by weight of a B monomer having a $T_g$ of >20° C. is present, and when said C macromer is present in an amount of 35 percent by weight or less, then at least 5 percent by weight of a B monomer having a $T_g$ of <0° C. is present, and wherein any B monomer present, if hydrophobic, is present in an amount up to 25 percent by weight, each said amounts being based on the total weight of the components A, B and C, said adhesive exhibiting a tackifier or plasticizer-free Polyken probe tack value of at least 300 gm/cm$^2$ as determined by ASTM D2979, a peel adhesion value of at least 20 oz/in as determined by PSTC 1, and a shear holding value of greater than 5 minutes as determined at 500 grams according to PSTC 7.

2. The adhesive of claim 1 wherein said A monomer is present in an amount of from 25 to 70 percent by weight, said B monomer is present in an amount of from 0 to 40 percent by weight, and said C macromer is present in an amount of from 10 to 65 percent by weight, based on the total weight of the respective components A, B and C.

3. The adhesive of claim 2 wherein said C macromer is present in an amount of at least 35 percent by weight.

4. The adhesive of claim 1 wherein the weight ratio of C macromer to monomers A and B present in said adhesive ranges from about 35:65 to 65:35.

5. The adhesive of claim 4 wherein the weight ratio of C macromer to monomers A and B present in said adhesive ranges from about 40:60 to 50:50.

6. The adhesive of claim 1 wherein said B monomer has a $T_g$ of >20° C. and is hydrophilic.

7. The adhesive of claim 1 wherein said A monomer is selected from the group consisting of hydroxy($C_{1-5}$)alkylacrylates, hydroxy($C_{1-5}$)alkyl methacrylates, dihydroxy($C_{1-5}$)alkyl acrylates, dihydroxy($C_{1-5}$)alkyl methacrylates and mixtures thereof.

8. The adhesive of claim 1 wherein said B monomer is a water-soluble vinyl monomer having at least one nitrogen atom.

9. The adhesive of claim 8 wherein said B monomer is selected from the group consisting of N-mono-substituted acrylamides, N,N-disubstituted acrylamides and mixtures thereof.

10. The adhesive of claim 1 wherein said macromer is defined by the formula $X\text{-}(Y)_p\text{-}Z\text{-}R$, wherein X is a moiety copolymerizable with monomers A and B or capable of attachment to copolymerized monomers A and B, Y is a divalent linking group, Z is a water-soluble or water-dispersible homo- or copolymeric moiety, R is a terminal group, and p is 0 or 1.

11. The adhesive of claim 10 wherein X is a (meth)acrylate moiety.

12. The adhesive of claim 11 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

13. The adhesive of claim 1 wherein said macromer is defined by the formula:

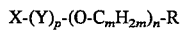

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

14. The adhesive of claim 13 wherein the macromer is defined by the formula:

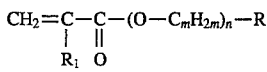

wherein $R_1$ is hydrogen or $C_{1-5}$ alkyl and R is a terminal group.

15. The adhesive of claim 14 wherein n is an integer of from 5 to 30.

16. The adhesive of claim 14 wherein R is OH or $C_{1-5}$ alkyl.

17. The adhesive of claim 1 wherein said copolymer comprises an hydroxy($C_{1-5}$)alkyl acrylate A monomer copolymerized with acrylamide, butyl acrylate, vinyl pyrrolidone and acrylic acid as B monomers, and a water-soluble or water-dispersible macromer.

18. The adhesive of claim 1 wherein any B monomer present, if hydrophobic, is present in an amount up to 15 percent by weight, based on the total weight of the respective components A, B and C.

19. The adhesive of claim 1 wherein a B monomer is present which comprises a monomeric acrylic or methacrylic acid ester of a non-tertiary alcohol having from 4–12 carbon atoms on average.

20. The adhesive of claim 1, wherein said B monomer is a vinyl monomer selected from the group consisting of acrylic acid, methacrylic acid, methoxyethyl acrylate, methoxyethyl methacrylate, ethoxyethyl acrylate, ethoxyethyl methacrylate, methyl acrylate, methyl methacrylate, ethyl acrylate, ethyl methacrylate, propyl acrylate, propyl methacrylate, n-butyl acrylate, n-butyl methacrylate, vinyl pyrrolidone, vinyl caprolactam and mixtures thereof.

21. The adhesive of claim 1 wherein said macromer is selected from the group consisting of ethoxylated hydroxy ($C_{1-5}$ alkyl) acrylate, propoxylated hydroxy ($C_{1-5}$ alkyl) acrylate, ethoxylated hydroxy ($C_{1-5}$ alkyl) methacrylate, and propoxylated ($C_{1-5}$ alkyl) methacrylate.

22. The adhesive of claim 1 wherein said macromer is selected from the group consisting of ethoxylated and propoxylated hydroxy ($C_{1-5}$ alkyl) (meth) acrylate, poly(2-ethyl- 2-oxazoline), polyacrylic acid, polyvinyl alcohol, polyvinyl pyrrolidone, polyvinyl caprolactam and polymethylvinyl ether mono (meth) acrylate.

* * * * *